US006866822B1

(12) United States Patent
House et al.

(10) Patent No.: US 6,866,822 B1
(45) **Date of Patent: *Mar. 15, 2005**

(54) GIMBALED BLADDER ACTUATOR FOR USE WITH TEST STRIPS

(75) Inventors: Allen House, Danville, CA (US); Lorin Olson, Scotts Valley, CA (US)

(73) Assignee: Lifescan, Inc., Milpitas, CA (US)

( * ) Notice: Subject to any disclaimer, the term of this patent is extended or adjusted under 35 U.S.C. 154(b) by 17 days.

This patent is subject to a terminal disclaimer.

(21) Appl. No.: 09/637,504

(22) Filed: Aug. 11, 2000

(51) Int. Cl.[7] ............................ G01N 33/48; B01L 9/00

(52) U.S. Cl. ....................... 422/82.05; 422/55; 422/102; 436/48; 436/165

(58) Field of Search .................... 422/61, 99, 101–104, 422/82.05, 55; 436/43, 46, 48, 165; 356/244, 36

(56) References Cited

U.S. PATENT DOCUMENTS

| | | | | |
|---|---|---|---|---|
| 3,620,676 A | | 11/1971 | Davis | |
| 3,640,267 A | | 2/1972 | Hurtig et al. | |
| 4,088,448 A | | 5/1978 | Lilja et al. | |
| 4,426,451 A | | 1/1984 | Columbus | |
| 4,480,685 A | | 11/1984 | Gilbertson | |
| 4,868,129 A | | 9/1989 | Gibbons et al. | |
| 5,104,813 A | | 4/1992 | Besemer et al. | |
| 5,208,163 A | | 5/1993 | Charlton et al. | |
| 5,230,866 A | | 7/1993 | Shartle et al. | |
| 5,252,044 A | | 10/1993 | Raines et al. | |
| 5,302,093 A | | 4/1994 | Owens et al. | |
| 5,309,176 A | | 5/1994 | Faes et al. | |
| 5,700,695 A | | 12/1997 | Yassinzadeh et al. | |
| 5,736,404 A | * | 4/1998 | Yassinzadeh et al. | 436/52 |
| 6,652,814 B1 | * | 11/2003 | House et al. | 422/104 |
| 2003/0044318 A1 | * | 3/2003 | Olson | 422/58 |

FOREIGN PATENT DOCUMENTS

| | | |
|---|---|---|
| EP | 0374115 A1 | 6/1990 |
| EP | 0803288 A2 | 4/1997 |
| EP | 803288 | 10/1997 |
| WO | WO 95/12117 | 5/1995 |
| WO | WO99/34957 | 7/1999 |

OTHER PUBLICATIONS

Gimbal definition from English Oxford Dictionary online: http://dictionary.oed.com/cgi/entry/00094657?signle=1&query_type=work&queryword=gimbal&edition=2e&first=1&max to show=10.

* cited by examiner

*Primary Examiner*—Lyle A. Alexander

(57) ABSTRACT

Gimbaled bladder actuators and methods for their use in compressing bladders present on test strips are provided. The subject actuators are characterized by the presence of a gimbaled compression pad under movement control of an actuating means, preferably an automated actuating means. Also provided are meters for reading test strips that include bladders, where the meters include the subject gimbaled bladder actuators.

15 Claims, 9 Drawing Sheets

SECTION B-B

GIMBALED BLADDER ACTUATOR FOR USE WITH TEST STRIPS

FIELD OF THE INVENTION

The field of this invention is fluidic medical diagnostic devices for measuring the concentration of an analyte in or a property of a biological fluid.

BACKGROUND OF THE INVENTION

A variety of medical diagnostic procedures involve tests on biological fluids, such as blood, urine, or saliva, and are based on a change in a physical characteristic of such a fluid or an element of the fluid, such as blood serum. The characteristic can be an electrical, magnetic, fluidic, or optical property. When an optical property is monitored, these procedures may make use of a transparent or translucent device to contain the biological fluid and a reagent. A change in light absorption of the fluid can be related to an analyte H concentration in, or property of, the fluid.

In many such devices, fluid is introduced into the device at one location but analyzed at another. In such devices, movement of the introduced fluid from the introduction location to the measurement location is necessary. As such, these devices require a means for moving fluid from the introduction site to the measurement site.

A variety of different design configurations have been developed to provide for this fluid movement. One type of device relies on capillary action to move fluid through the device, where the fluid paths through the device are dimensioned to provide for this capillary action. Other designs include those intended for use with gravity, those intended for use with injection of the sample under pressure, and the like.

In one class of fluidic test devices or strips that find use in various assay applications, fluid is moved through the device from the point of introduction by negative pressure, where the negative pressure is typically provided by a compressible bladder. Such devices include those described in U.S. Pat. No. 3,620,676; U.S. Pat. No. 3,640,267 and EP 0 803 288.

With these types of devices, there is a need to be able to actuate the bladder in a reproducible and uniform manner, such that errors in the assay are not introduced through variations in bladder volume through the compression and decompression cycle.

Relevant Literature

References of interest include: U.S. Pat. Nos. 3,620,676; 3,640,267; 4,088,448; 4,426,451; 4,868,129; 5,104,813; 5,230,866; 5,700,695; 5,736,404; 5,208,163; and European Patent Application EP 0 803 288.

SUMMARY OF THE INVENTION

Gimbaled bladder actuators and methods for their use in compressing bladders present on fluidic devices or test strips are provided. The actuators are characterized by the presence of a gimbaled compression pad under movement control of an actuating means, preferably an automated actuating means. Also provided are meters for reading test strips that include bladders, where the meters include the subject gimbaled bladder actuators.

DESCRIPTION OF THE SPECIFIC EMBODIMENTS

Figure 1:
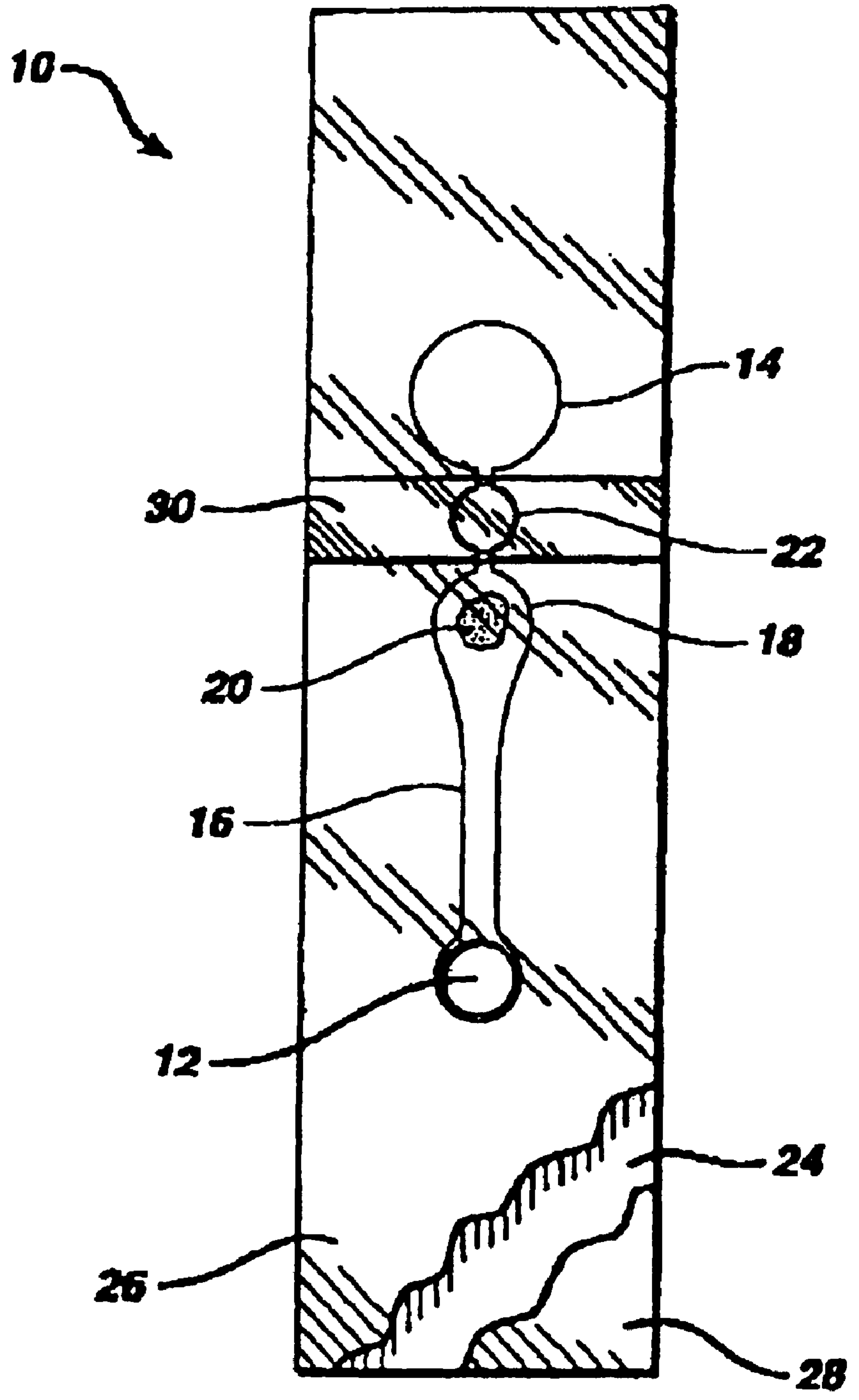
FIG. 1 is a plan view of a test strip which includes a bladder that may be actuated by the subject gimbaled bladder actuators.

Gimbaled bladder actuators and methods for their use in compressing bladders present on test strips are provided. The subject actuators are characterized by the presence of a gimbaled compression pad under movement control of an actuating means, preferably an automated actuating means. Also provided are meters for reading bladder including test strips, where the meters include the subject gimbaled bladder actuating devices. In further describing the subject invention, the subject gimbaled bladder actuators are described first in greater detail, followed by a description of the test strip/meter systems with which the subject gimbaled bladder actuator find use, as well as methods for using the same.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

As summarized above, the subject invention provides bladder compressing devices or actuators that find use in compressing bladders on fluidic devices or test strips that include bladders. In further describing the subject devices, the subject bladder actuators will be described first in general terms, followed by a detailed discussion of a representative actuator in terms of the figures.

A feature of the subject bladder compressing devices or actuators is that they include a gimbaled compression pad. As such, the subject bladder actuators are gimbaled bladder actuators. By gimbaled compression pad is meant a planar compression element that is suspended from a holder in a manner such that the planar compression element becomes parallel to the surface it contacts during actuation. By planar compression element is meant a rigid piece having a substantially planar surface. The view normal to the planar surface of this element may have varying area configurations, including circular, square, rectangular, trapezoidal, oval, triangular, irregular, etc., and in many embodiments is selected so as to contact substantially all of the upper surface of a bladder of a test strip or fluidic device with which the gimbaled bladder actuator is employed. The actual area of the planar surface may vary, but is generally at least about 0.008 square inches, usually at least about 0.15 square inches and more usually at least about 0.2 square inches, where the actual area may be as great as 0.4 square inches or greater, but generally does not exceed about 0.6 square inches and usually does not exceed about 0.8 square inches. In certain embodiments, the actual area ranges from about 0.15 to 0.25 square inches, usually from about 0.19 to 0.21 square inches.

The gimbaled compression pad is characterized by being capable of applying uniform pressure to the bladder upon actuation. By uniform pressure is meant that the pressure applied by the planar compression element at any two different locations on the bladder that is contacted by the compression element is substantially the same or identical. Where there is pressure variance, the magnitude of the variance at any two given locations typically does not exceed about 18 lbs per square inch, usually does not exceed about 7 lbs per square inch and more usually does not exceed about 2 lbs per square inches. The amount of force applied by the gimbaled pad to the bladder during use typically ranges in many embodiments from about 0.25 to 10, usually from about 0.5 to 5 and more usually from about 1.0 to 1.5 lbs.

Also present in the subject bladder compressing devices is an actuating means for actuating or moving the gimbaled compression pad onto and off of a bladder of present on a test strip. In principal, any convenient actuating means may be employed that is capable of contacting the gimbaled compression pad against the bladder surface in a manner that applies substantially uniform pressure across the bladder surface, as described supra. Thus, the actuation means may be manual or automatic. Manual actuation means may simply be a compression button that can be pushed by an operator to achieve contact of the gimbaled compression pad and the bladder surface. In many preferred embodiments, the actuation means is an automated actuation means that is capable of contacting the bladder surface with the gimbaled compression pad in a reproducible manner.

While any convenient automated actuation means may be employed, one convenient automated actuation means includes the following elements: (i) a lever arm; (ii) a chassis; and (iii) a solenoid. In this representative automated actuation means, at one end of the lever arm the gimbaled compression pad (i.e. the planar compression element and the holder) is attached. The lever arm is such that it is capable of holding the gimbaled compression pad over, the bladder such that, upon actuation, the gimbaled compression pad contacts the bladder in a manner sufficient to compress the bladder, as described supra. The other end of the lever arm is connected to a chassis or analogous element. The length of the lever arm generally ranges from about 0.3 inches to 0.4 inches, usually from about 0.345 inches to 0.355 inches.

The chassis or analogous element provides for operative communication between the lever arm and the solenoid. The chassis may have any convenient configuration, where a representative configuration is provided in the figures, described infra.

Connected to the chassis is a solenoid actuator which is capable of moving the lever arm and therefore the gimbaled compression pad in the desired manner upon actuation. The solenoid is generally a dual action solenoid capable of moving the gimbaled compression pad in two directions: a first direction onto the bladder and a second direction off of the bladder. Generally, the solenoid is under the control of a solenoid actuation means, where the means may be manual (i.e. may actuate the solenoid following direct input from a human user) or automated (i.e. may automatically actuate the solenoid following detection of an event by a sensor in a device, such as a sample placement detecting sensor).

Figure 6A:
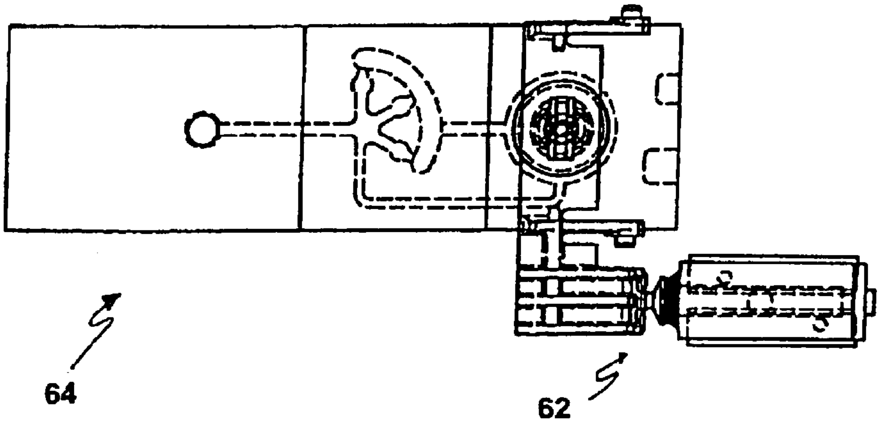
FIG. 6A provides a top view of a gimbaled bladder actuator according to the subject invention.
Figure 6B:
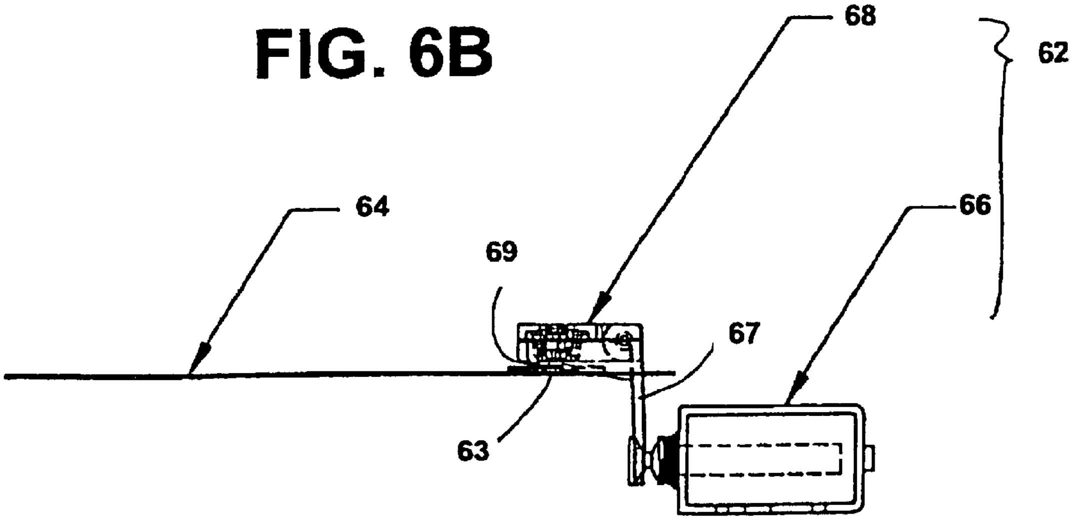
FIG. 6B shows a side view of the device shown in FIG. 6A.

Turning now to the figures, FIG. 6A provides a top view of a bladder compression device 62 of the subject invention positioned over a test strip 64 that includes a bladder. FIG. 6B shows a side view of the device shown in FIG. 6A. In FIG. 6B, bladder compression device is seen placed over the end of test strip 64. Bladder compression device 62 includes solenoid actuation means 66 and lever arm 68. Located on lever arm 68 is gimbaled compression pad 69, which is placed above bladder 63 of test strip 64.

Figure 7A:
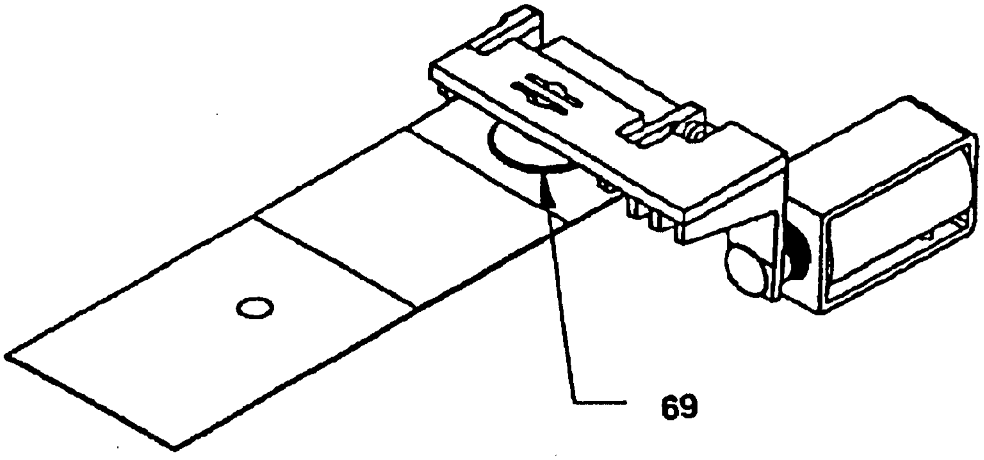
FIGS. 7A and 7B provide top and bottom perspective views of the device shown in FIGS. 6A and 6B.
Figure 7B:
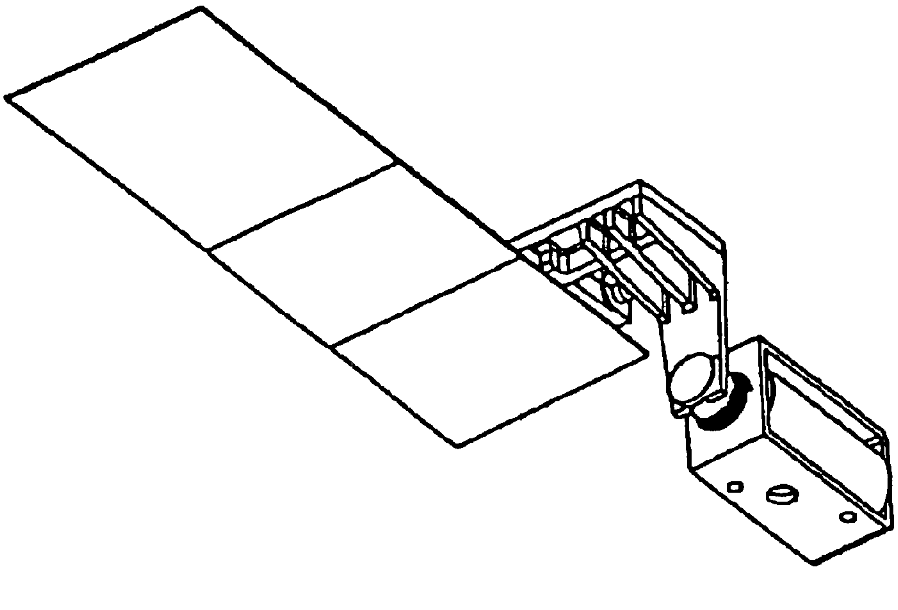

FIG. 7A and FIG. 7B provide top and bottom perspective views of the device shown in FIGS. 6A and 6B. Gimbaled compression pad 69 can be seen in FIG. 7A.

Figure 8A:
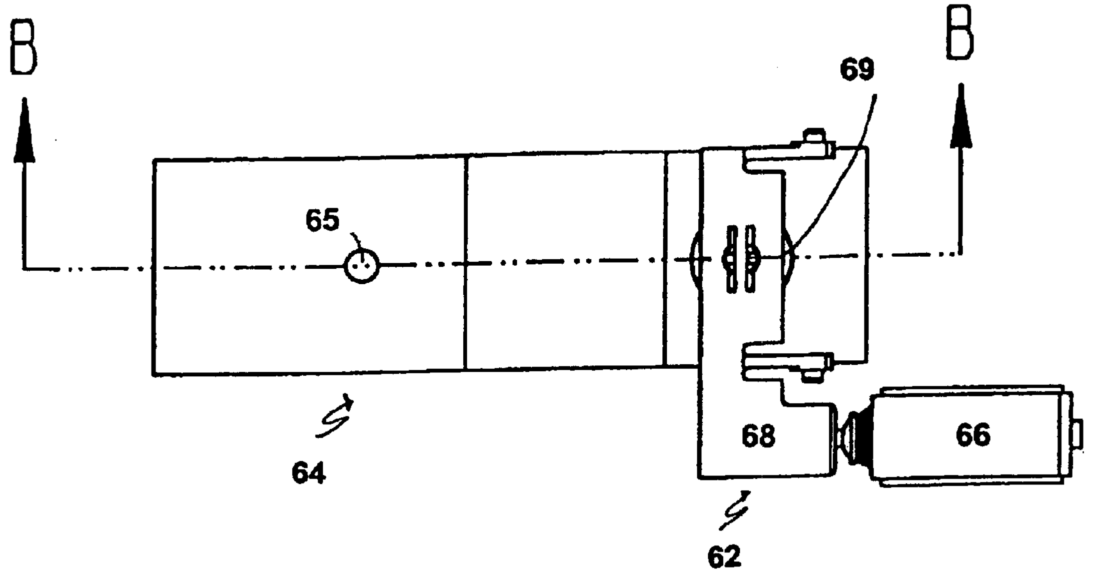
FIG. 8A provides a top perspective view of the device shown in FIG. 6A, while FIG. 8B provides a view along line B—B of FIG. 8A and FIG. 8C provides a blow-up view of FIG. 8B.
Figure 8B:
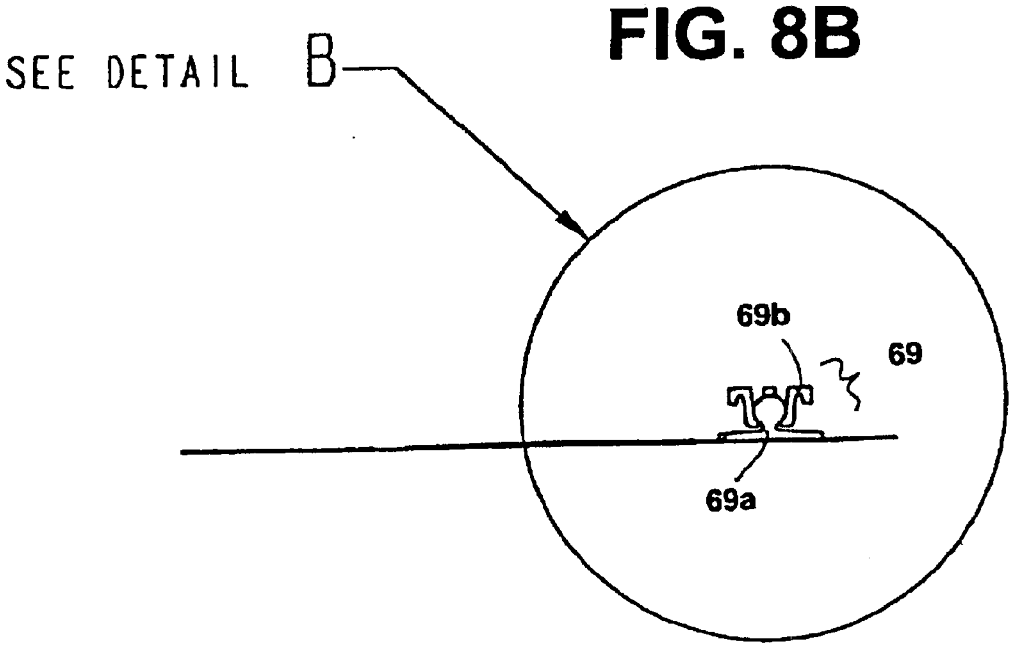
Figure 8C:
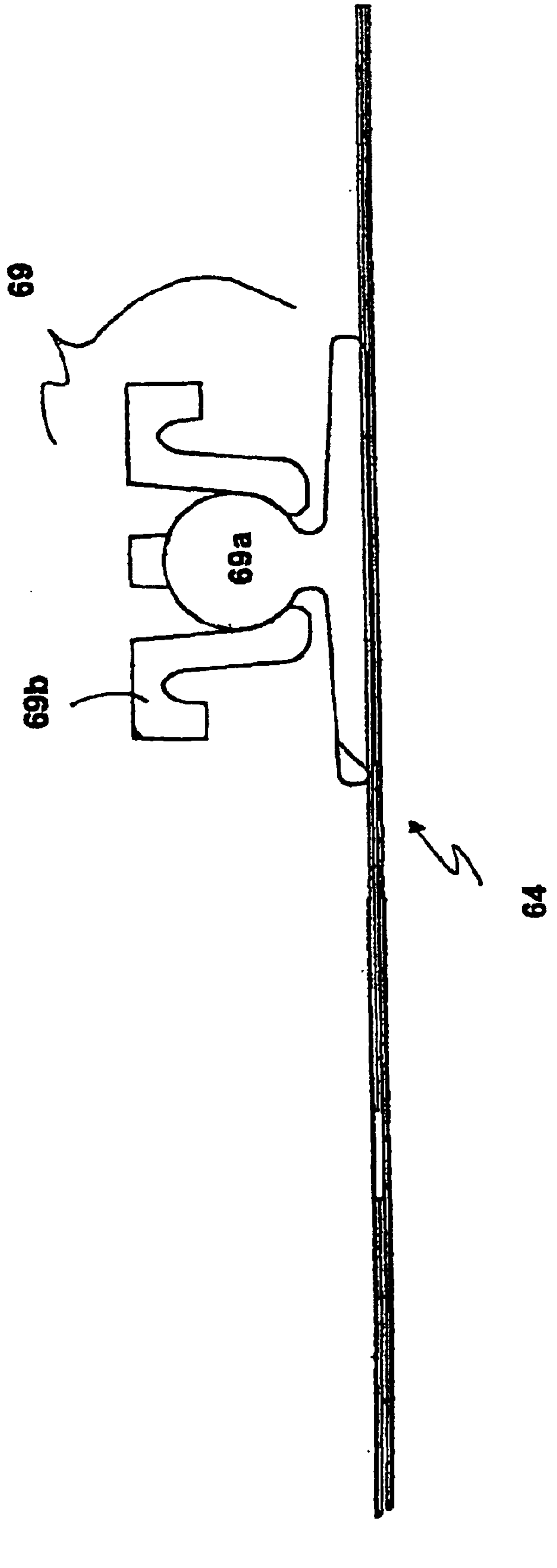

FIG. 8A provides a top perspective view of the device shown in FIG. 6A. In FIG. 8A, bladder compression device 62 is positioned over test strip 64. The top of solenoid 66 and lever arm 68 is visible, as well as gimbaled compression pad 69. Also visible is sample application region 65 of test strip 64. FIG. 8B provides a blow up view along line B—B showing gimbaled compression pad 69. Gimbaled compression pad 69 is made up of planar compression element 69*a* in holder 69*b*. FIG. 8C provides a blow-up view of FIG. 8A, showing gimbaled compression pad 69 positioned over test strip 64.

Systems

The above described gimbaled bladder compressing devices or actuators find use in systems made up of test strips and meters, as described in greater detail below.

Test Strips

The test strips with which the subject gimbaled bladder actuators find use are fluidic devices that generally include a sample application area; a bladder, to create a suction force to draw the sample into the device; a measurement area, in which the sample may undergo a change in an optical parameter, such as light scattering; and a stop junction to precisely stop flow after filling the measurement area. Preferably, the test strip is substantially transparent over the measurement area, so that the area can be illuminated by a light source on one side and the transmitted light measured on the opposite side.

Figure 2:
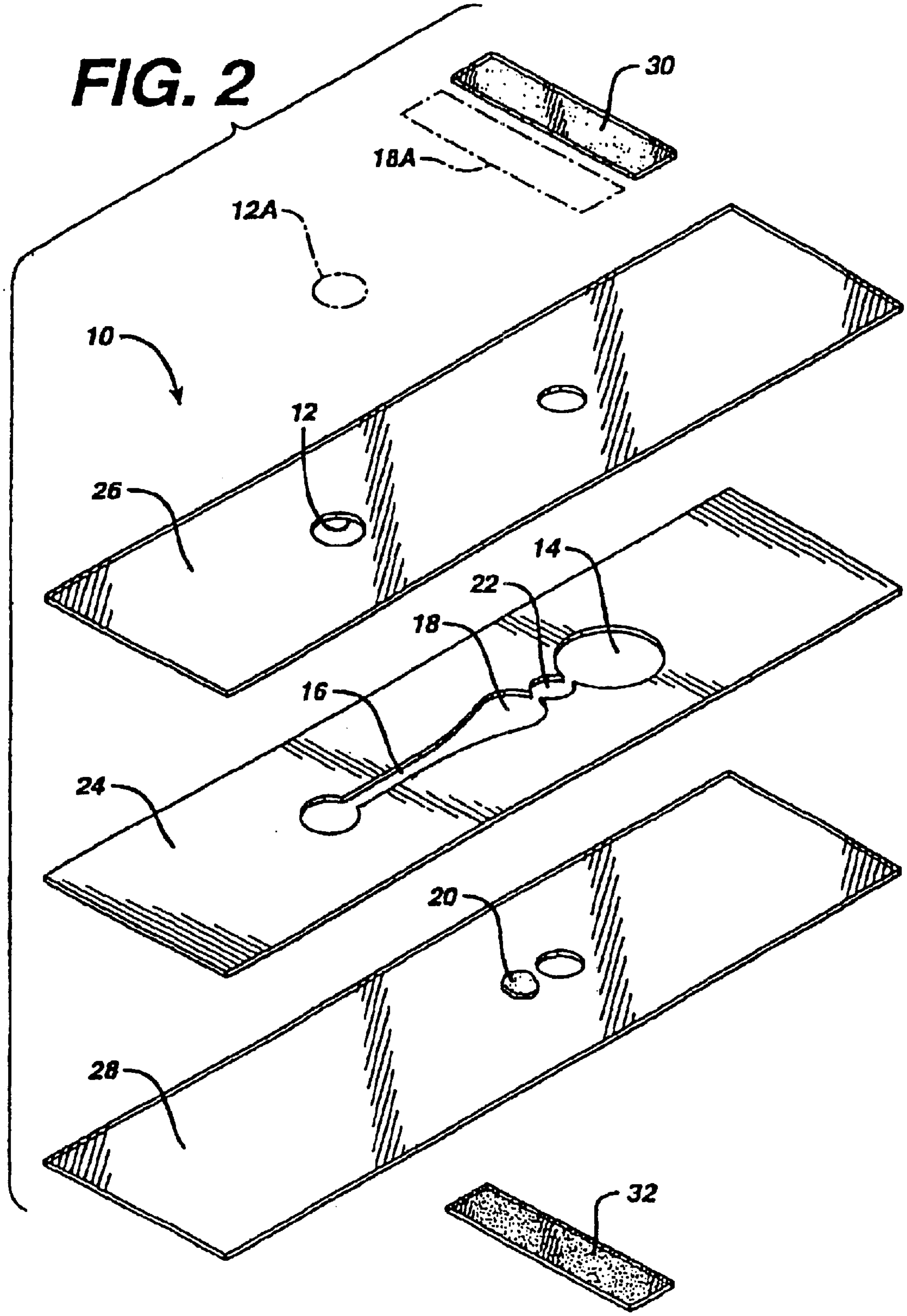
FIG. 2 is an exploded view of the device of FIG. 1.
Figure 3:
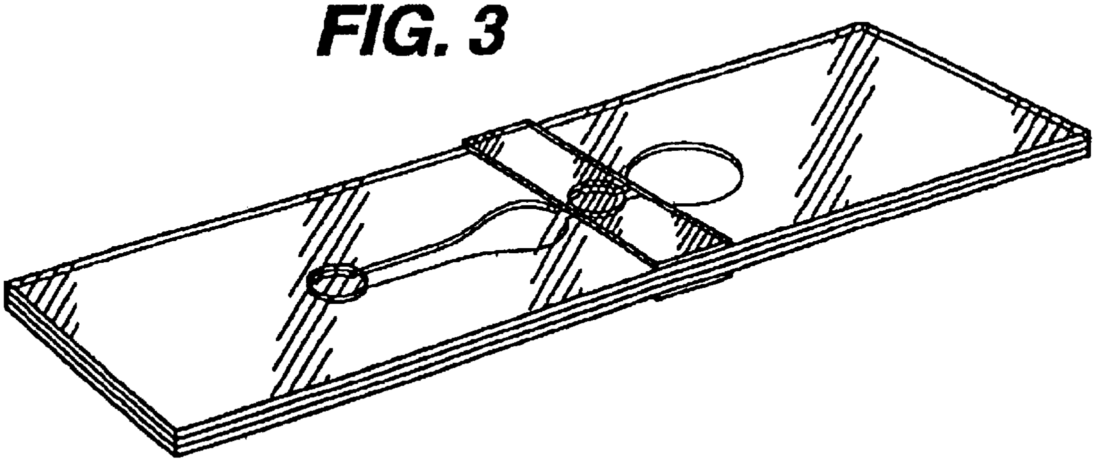
FIG. 3 is a perspective view of the device of FIG. 1.

A representative test strip with which the subject gimbaled bladder actuators find use is shown in FIGS. 1, 2 and 3. FIG. 1 provides a plan view of representative device 10, while FIG. 2 provides an exploded view and FIG. 3 provides a perspective view of the same representative device. Sample is applied to sample port 12 after bladder 14 has been compressed. Clearly, the region of layer 26 and/or layer 28 that adjoins the cutout for bladder 14 must be resilient, to permit bladder 14 to be compressed. Polyester of about 0.1 mm thickness has suitable resilience and springiness. Preferably, top layer 26 has a thickness of about 0.125 mm, bottom layer 28 about 0.100 mm. When the bladder is released, suction draws sample through channel 16 to measurement area 18, which preferably contains a reagent 20. In order to ensure that measurement area 18 can be filled with sample, the volume of bladder 14 is preferably at least about equal to the combined volume of channel 16 and measurement area 18. If measurement area 18 is to be illuminated from below, layer 28 must be transparent where it adjoins measurement area 18.

As shown in FIGS. 1, 2, and 3, stop junction 22 adjoins bladder 14 and measurement area 18; however, a continuation of channel 16 may be on either or both sides of stop junction 22, separating the stop junction from measurement area 18 and/or bladder 14. When the sample reaches stop junction 22, sample flow stops. The principle of operation of stop junctions is described in U.S. Pat. No. 5,230,866, incorporated herein by reference.

As shown in FIG. 2, all the above elements are formed by cutouts in intermediate layer 24, sandwiched between top layer 26 and bottom layer 28. Preferably, layer 24 is double-sided adhesive tape. Stop junction 22 is formed by an additional cutout in layer 26 and/or 28, aligned with the cutout in layer 24 and sealed with sealing layer 30 and/or 32. Preferably, as shown, the stop junction comprises cutouts in both layers 26 and 28, with sealing layers 30 and 32. Each cutout for stop junction 22 is at least as wide as channel 16. Also shown in FIG. 2 is an optional filter 12A to cover sample port 12. The filter may separate out red blood cells from a whole blood sample and/or may contain a reagent to interact with the blood to provide additional information. A suitable filter comprises an anisotropic membrane, preferably a polysulfone membrane of the type available from Spectral Diagnostics, Inc., Toronto, Canada Optional reflector 18A may be on, or adjacent to, a surface of layer 26 and positioned over measurement area 18. If the reflector is present, the device becomes a transflectance device.

The test strip pictured in FIG. 2 and described above is preferably formed by laminating thermoplastic sheets 26 and 28 to a thermoplastic intermediate layer 24 that has adhesive on both of its surfaces. The cutouts that form the elements shown in FIG. 1 may be formed, for example, by laser- or die-cutting of layers 24, 26, and 28. Alternatively, the device can be formed of molded plastic. Preferably, the surface of sheet 28 is hydrophilic. (Film 9962, available from 3M, St. Paul, Minn.) However, the surfaces do not need to be hydrophilic, because the sample fluid will fill the device without capillary forces. Thus, sheets 26 and 28 may be untreated polyester or other thermoplastic sheet, well known in the art. Similarly, since gravity is not involved in filling, the device can be used in any orientation. Unlike capillary fill devices that have vent holes through which sample could leak, these types of devices vent through the sample port before sample is applied, which means that the part of the strip that is first inserted into the meter is without an opening, reducing the risk of contamination.

Other fluidic device configurations are also possible, where such alternative device configurations include those that have: (a) a bypass channel; (b) multiple parallel measurement areas; and/or (c) multiple in series measurement areas; etc. In addition, the above described laminated structures can be adapted to injection molded structures. A variety of alternative fluidic devices with which the subject gimbaled bladder compressing devices may find use are described in co-pending application Ser. Nos. 09/333,765, filed Jun. 15, 1999; and Ser. No. 09/356,248, filed Jul. 16, 1999, the disclosures of which are herein incorporated by reference.

Meters

Figures 4, 4A:
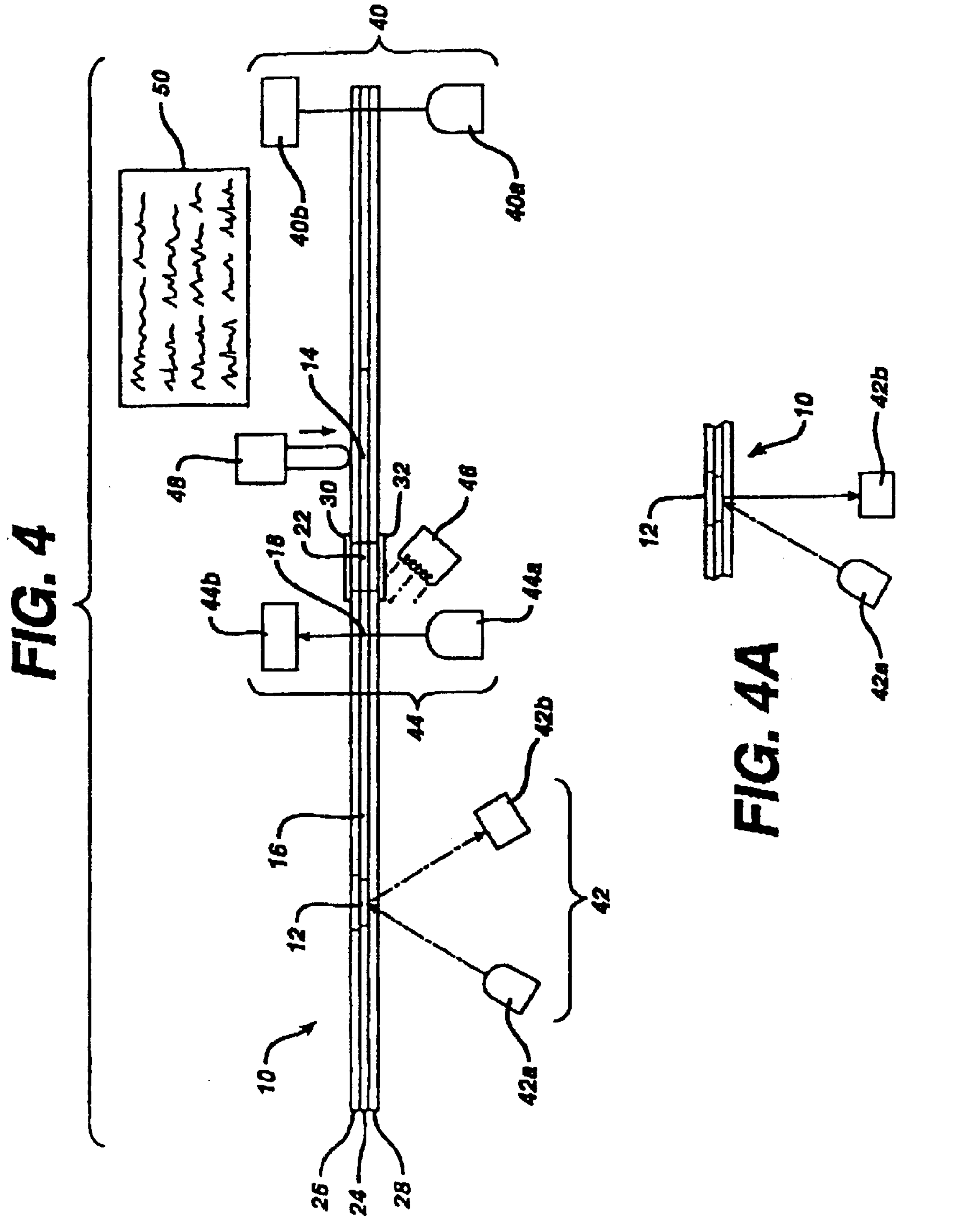
FIG. 4 is a schematic of a meter that includes a gimbaled bladder actuator according to the subject invention.
FIG. 4A depicts an alternative embodiment of an element of the meter of FIG. 4.

The subject gimbaled bladder actuators find use in meters, generally automated meters, that are designed for use with the above described test strips. A representative meter is depicted in FIG. 4, where a representative test strip 10 is inserted into the meter. The meter shown in FIG. 4 includes strip detector 40 (made up of LED 40*a* and detector 40*b*), sample detector 42 (made up of light source 42*a* and detector 42*b*), measurement system 44 (made up of LED 44*a* and detector 44*b*), and optional heater 46. The device further includes a gimbaled bladder actuator 48, which is described in greater detail supra. The gimbaled bladder actuator is, in many embodiments, actuated by the strip detector 40 and the sample detector 42, such that when a strip is inserted into the meter and detected by the strip detector, the gimbaled bladder actuator is depressed, and when the sample is added to the fluidic device or strip inserted into the meter, the gimbaled bladder actuator is withdrawn so as to decompress the bladder and concomitantly pull sample into the measurement area of the device via the resultant negative pressure conditions in the fluid channel(s) of the test strip. Also present is a meter display 50 that provides for an interface with the user.

Methods of Use

The above described test strip/meter systems that include the subject gimbaled bladder actuators are suitable for use in a variety of analytical tests of biological fluids, such as determining biochemical or hematological characteristics, or measuring the concentration in such fluids of analytes such as proteins, hormones, carbohydrates, lipids, drugs, toxins, gases, electrolytes, etc. The procedures for performing these tests have been described in the literature. Among the tests, and where they are described, are the following: (1) Chromogenic Factor XIIa Assay (and other clotting factors as well): Rand, M. D. et al., Blood, 88, 3432 (1996); (2) Factor X Assay: Bick, R. L. Disorders of Thrombosis and Hemostasis: Clinical and Laboratory Practice. Chicago, ASCP Press, 1992; (3) DRVVT (Dilute Russells Viper Venom Test): Exner, T. et al., Blood Coag. Fibrinol, 1, 259 (1990); (4) Immunonephelometric and Immunoturbidimetric Assays for Proteins: Whicher, J. T., CRC Crit. Rev. Clin Lab Sci. 18:213 (1983); (5) TPA Assay: Mann, K. G., et al., Blood, 76, 755, (1990); and Hartshorn, J. N. et al., Blood, 78, 833 (1991); (6) APTT (Activated Partial Thromboplastin Time Assay): Proctor, R. R. and Rapaport, S. I. Amer. J. Clin. Path, 36, 212 (1961); Brandt, J. T. and Triplett, D. A. Amer. J. Clin. Path., 76, 530 (1981); and Kelsey, P. R. Thromb. Haemost. 52, 172 (1984); (7) HbAlc Assay (Glycosylated Hemoglobin Assay): Nicol, D. J. et al., Clin. Chem. 29, 1694 (1983); (8) Total Hemoglobin: Schneck et al., Clinical Chem., 32/33, 526 (1986); and U.S. Pat. No. 4,088,448; (9) Factor Xa: Vinazzer, H., Proc. Symp. Dtsch. Ges. Klin. Chem., 203 (1977), ed. By Witt, I; (10) Colorimetric Assay for Nitric Oxide: Schmidt, H. H., et al., Biochemica, 2, 22 (1995).

The above described test strip/meter systems are particularly well suited for measuring blood-clotting time—"prothrombin time" or "PT time," as more fully described in U.S. Pat. No. 6,521,182, filed Jun. 15, 1999; and U.S. Pat. No. 6,261,519, filed Jul. 16, 1999; the disclosures of which are herein incorporated by reference. The modifications needed to adapt the device for applications such as those listed above require no more than routine experimentation.

In using the above systems that include the subject gimbaled bladder actuator, the first step the user performs is to turn on the meter, thereby energizing strip detector 40, sample detector 42, measurement system 44, and optional heater 46. The second step is to insert the strip. Preferably, the strip is not transparent over at least a part of its area, so that an inserted strip will block the illumination by LED 40*a* of detector 40*b*. (More preferably, the intermediate layer is formed of a non-transparent material, so that background light does not enter measurement system 44.) Detector 40*b* thereby senses that a strip has been inserted and triggers gimbaled bladder actuator 48 to compress bladder 14. A meter display 50 then directs the user to apply a sample to sample port 12 as the third and last step the user must perform to initiate the measurement sequence. The empty sample port is reflective. When a sample is introduced into the sample port, it absorbs light from LED 42*a* and thereby reduces the light that is reflected to detector 42*b*. That reduction in light, in turn, signals gimbaled bladder actuator 48 to release bladder 14. The resultant suction in channel 16 draws sample through measurement area 18 to stop junction 22. Light from LED 44*a* passes through measurement area 18, and detector 44*b* monitors the light transmitted through the sample as it is clotting. Analysis of the transmitted light as a function of time (as described below) permits a calculation of the PT time, which is displayed on the meter display 50. Preferably, sample temperature is maintained at about 39° C. by heater 46.

As described above, the detector senses a sample in sample port 12, simply by detecting a reduction in (specular) reflection of a light signal that is emitted by 42*a* and detected by 42*b*. However, that simple system cannot easily distinguish between a whole blood sample and some other liquid (e.g., blood serum) placed in the sample port in error or, even, an object (e.g., a finger) that can approach sample port 12 and cause the system to erroneously conclude that a proper sample has been applied. To avoid this type of error, another embodiment measures diffuse reflection from the sample port. This embodiment appears in FIG. 4A, which shows detector 42*b* positioned normal to the plane of strip 10. With the arrangement shown in FIG. 4A, if a whole blood sample has been applied to sample port 12, the signal detected by 42*b* increases abruptly, because of scattering in the blood sample, then decreases, because of rouleaux formation. The detector system 42 is thus programmed to require that type of signal before causing gimbaled bladder actuator 48 to release bladder 14. The delay of several seconds in releasing bladder 14 does not substantially affect the readings described below.

Figure 5:
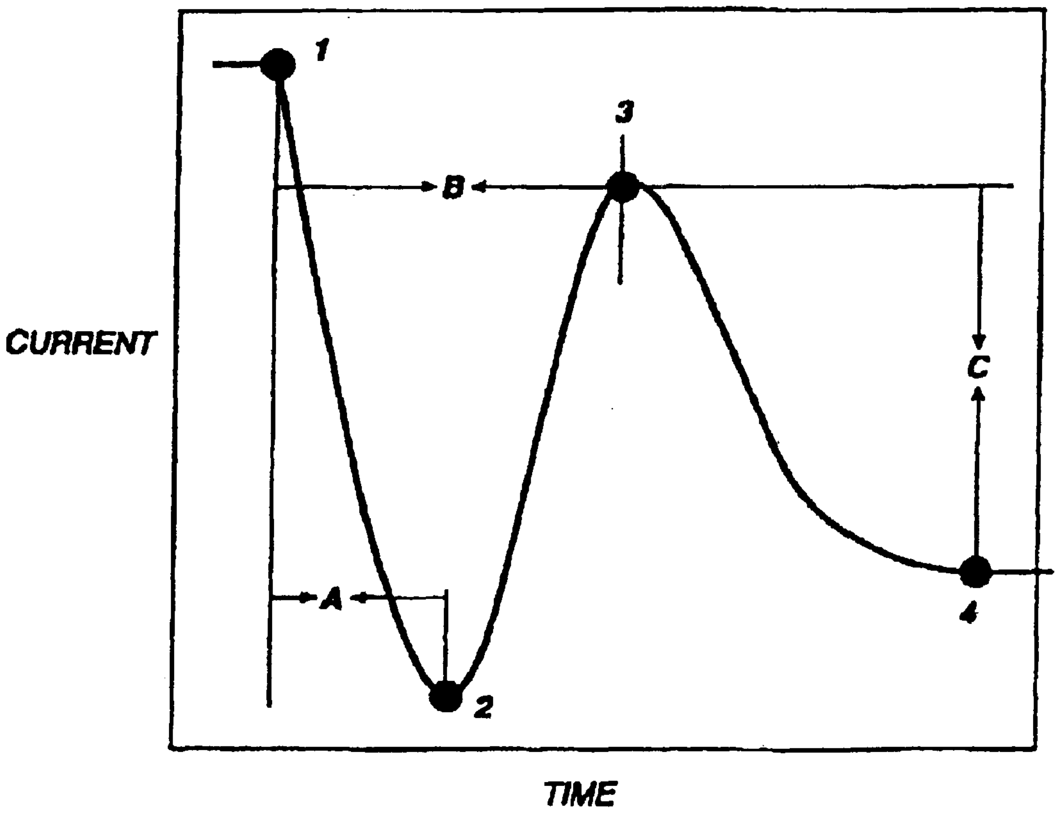
FIG. 5 is a graph of data that is used to determine PT time.

FIG. 5 depicts a typical "clot signature" curve in which the current from detector 44*b* is plotted as a function of time. Blood is first detected in the measurement area by 44*b* at time 1. In the time interval A, between points 1 and 2, the blood fills the measurement area. The reduction in current during that time interval is due to light scattered by red cells and is thus an approximate measure of the hematocrit. At point 2, sample has filled the measurement area and is at rest, its movement having been stopped by the stop junction. The red cells begin to stack up like coins (rouleaux formation). The rouleaux effect allows increasing light transmission through the sample (and less scattering) in the time interval between points 2 and 3. At point 3, clot formation ends rouleaux formation and transmission through the sample reaches a maximum. The PT time can be calculated from the interval B between points 1 and 3 or between 2 and 3. Thereafter, blood changes state from liquid to a semi-solid gel, with a corresponding reduction in light transmission. The reduction in C current C between the maximum 3 and endpoint 4 correlates with fibrinogen in the sample.

It is evident from the above results and discussion that the subject invention provides a means for applying uniform and reproducible bladder compression and decompression in test strips that include bladders. As such, the subject devices provide for the elimination of a source of error in analytical assays using such test strips. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A meter adapted to receive a test strip including a bladder, wherein said meter comprises a gimbaled bladder actuator, said gimbaled bladder actuator comprising:

a gimbaled compression pad comprising a holder and a compression member including a substantially planar compression element wherein said holder is attached to said meter at a gimbaled interface; and an actuator in contact with said holder for contacting said gimbaled compression pad with said bladder in a manner sufficient to compress said bladder by movement of said actuator when said test strip is positioned in said meter.

2. The gimbaled bladder actuator according to claim 1, wherein said actuator comprises a lever arm under the control of an automatic movement means.

3. The gimbaled bladder actuator according to claim 2, wherein said automatic movement means comprises a solenoid.

4. The gimbaled bladder actuator according to claim 2, wherein said lever arm is attached to said movement means by a chassis.

5. A meter adapted to receive a test ship including a bladder, wherein said meter comprises a gimbaled bladder actuator, said gimbaled bladder actuator comprising:

(a) a gimbaled compression pad comprising a holder and a compression member including a substantially planar compression element wherein said holder is attached to said meter at a gimbaled surface; and (b) actuator in contact with said holder for contacting said gimbaled compression pad with said bladder in a manner sufficient to compress said bladder by movement of said actuator when said test strip is positioned in said meter, wherein said actuating means comprises:

(i) a lever arm;

(ii) a chassis; and (iii) a solenoid.

6. The gimbaled bladder actuator according to claim 5, wherein said gimbaled compression pad has an actual area ranging from about 0.19 square inches to 0.21 square inches.

7. The gimbaled bladder actuator according to claim 5, wherein said arm moves said gimbaled compression pad against a bladder in a manner sufficient to apply uniform pressure to said bladder.

8. The gimbaled bladder actuator according to claim 5, wherein said gimbaled compression pad is capable of placing a compressive force on a bladder ranging from about 1 lb to about 1.5 lb.

9. An automatic meter for reading a test strip including a bladder, said meter comprising:

a gimbaled bladder actuator, wherein said gimbaled bladder actuator comprises:

(a) a gimbaled compression pad comprising a holder and a compression member including a substantially planar compression element wherein said holder is attached to said meter at a gimbaled interface; and (b) an actuator in contact with said holder for contacting said gimbaled compression pad with said bladder in a manner sufficient to compress said bladder by movement of said actuator when said test strip is positioned in said meter.

10. The automatic meter according to claim 9, wherein said actuator comprises a lover arm under the control of an automatic movement means.

11. The automatic meter according to claim 10, wherein said automatic movement means is a solenoid movement means.

12. The automatic meter according to claim 10, wherein said lever arm is attached to said movement means by a chassis.

13. The automatic meter according to claim 9, wherein said gimbaled compression pad has an actual area ranging from about 0.19 square inches to 0.21 square inches.

14. The automatic meter according to claim 9, wherein said arm moves said gimbaled compression pad against a bladder in a manner sufficient to apply uniform pressure to said bladder.

15. The automatic meter according to claim 9, wherein said gimbaled compression pad is capable of placing a compressive force on a bladder ranging from about 1 lb to 1.5 lb.

* * * * *